US011229395B2

(12) United States Patent
Bar-Tal et al.

(10) Patent No.: US 11,229,395 B2
(45) Date of Patent: Jan. 25, 2022

(54) DOUBLE BIPOLAR CONFIGURATION FOR ATRIAL FIBRILLATION ANNOTATION

(71) Applicant: Biosense Webster (Israel) Ltd., Yokneam (IL)

(72) Inventors: Meir Bar-Tal, Haifa (IL); Richard P. M. Houben, Lanaken (BE); Yaniv Ben Zriham, Binyamina (IL); Assaf Pressman, Pardes Hanna-Karkur (IL); Roy Urman, Karkur (IL); Shmuel Auerbach, Kerem Maharal (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 165 days.

(21) Appl. No.: 16/267,877

(22) Filed: Feb. 5, 2019

(65) Prior Publication Data
US 2019/0167137 A1 Jun. 6, 2019

Related U.S. Application Data

(60) Division of application No. 15/380,340, filed on Dec. 15, 2016, now Pat. No. 10,238,309, which is a
(Continued)

(51) Int. Cl.
*A61B 5/361* (2021.01)
*A61B 5/00* (2006.01)
(Continued)

(52) U.S. Cl.
CPC .............. *A61B 5/361* (2021.01); *A61B 5/287* (2021.01); *A61B 5/30* (2021.01); *A61B 5/316* (2021.01);
(Continued)

(58) Field of Classification Search
None
See application file for complete search history.

(56) References Cited

U.S. PATENT DOCUMENTS 4,721,114 A   1/1988 Dufault et al.
5,546,951 A   8/1996 Ben-Haim
(Continued)

FOREIGN PATENT DOCUMENTS

EP   2656784 A1   10/2013
JP   H11-197128   7/1999
(Continued)

OTHER PUBLICATIONS

Australia Examination Report from Divisional application No. 2019202318 dated Nov. 7, 2019.
(Continued)

*Primary Examiner* — Kennedy Schaetzle
(74) *Attorney, Agent, or Firm* — Louis J. Capezzuto

(57) ABSTRACT

Catheterization of the heart is carried out by inserting a probe having electrodes into a heart of a living subject, recording a bipolar electrogram and a unipolar electrogram from one of the electrodes at a location in the heart, and defining a window of interest wherein a rate of change in a potential of the bipolar electrogram exceeds a predetermined value. An annotation is established in the unipolar electrogram, wherein the annotation denotes a maximum rate of change in a potential of the unipolar electrogram within the window of interest. A quality value is assigned to the annotation, and a 3-dimensional map is generated of a portion of the heart that includes the annotation and the quality value thereof.

8 Claims, 14 Drawing Sheets

Related U.S. Application Data continuation of application No. 14/585,828, filed on Dec. 30, 2014, now Pat. No. 9,554,718.

(60) Provisional application No. 61/932,877, filed on Jan. 29, 2014.

(51) Int. Cl.

| | | |
|---|---|---|
| *A61B 5/30* | (2021.01) | |
| *A61B 5/287* | (2021.01) | |
| *A61B 5/316* | (2021.01) | |
| *A61B 5/352* | (2021.01) | |
| *A61B 34/20* | (2016.01) | |
| *A61B 18/14* | (2006.01) | |
| *A61B 18/00* | (2006.01) | |

(52) U.S. Cl.
CPC ............ *A61B 5/352* (2021.01); *A61B 5/7203* (2013.01); *A61B 5/726* (2013.01); *A61B 5/7221* (2013.01); *A61B 5/7235* (2013.01); *A61B 34/20* (2016.02); *A61B 18/1492* (2013.01); *A61B 2018/0016* (2013.01); *A61B 2018/00267* (2013.01); *A61B 2018/00839* (2013.01); *A61B 2034/2051* (2016.02)

(56) References Cited

U.S. PATENT DOCUMENTS

| | | | |
|---|---|---|---|
| 5,738,096 A | 4/1998 | Ben-Haim | |
| 6,035,231 A | 3/2000 | Sornmo et al. | |
| 6,226,542 B1 | 5/2001 | Reisfeld | |
| 6,301,496 B1 | 10/2001 | Reisfeld | |
| 6,574,492 B1 | 6/2003 | Ben-Haim et al. | |
| 6,669,692 B1 | 12/2003 | Nelson et al. | |
| 6,690,963 B2 | 2/2004 | Ben-Haim et al. | |
| 6,892,091 B1 | 5/2005 | Ben-Haim et al. | |
| 8,467,863 B2 | 6/2013 | Kahlert | |
| 8,478,393 B2 | 7/2013 | Ramanathan et al. | |
| 8,700,136 B2 | 4/2014 | Rubinstein | |
| 8,838,216 B2 | 9/2014 | Frances et al. | |
| 10,238,309 B2 | 3/2019 | Bar-Tal et al. | |
| 2001/0056245 A1 | 12/2001 | Mlynash | |
| 2002/0055683 A1 | 5/2002 | Anderson | |
| 2002/0120206 A1* | 8/2002 | Taha | A61B 5/363 600/515 |
| 2003/0050563 A1 | 3/2003 | Suribhotla | |
| 2003/0083581 A1* | 5/2003 | Taha | A61B 5/349 600/509 |
| 2004/0059237 A1* | 3/2004 | Narayan | A61B 5/35 600/509 |
| 2004/0111033 A1* | 6/2004 | Oung | A61B 5/4035 600/483 |
| 2004/0133113 A1 | 7/2004 | Krishnan | |
| 2006/0136414 A1 | 6/2006 | Roach et al. | |
| 2007/0156056 A1 | 7/2007 | Min et al. | |
| 2007/0219454 A1 | 9/2007 | Guzzetta | |
| 2010/0094274 A1 | 4/2010 | Narayan et al. | |
| 2010/0191132 A1 | 7/2010 | Jackson | |
| 2010/0256699 A1 | 10/2010 | Makdissi | |
| 2011/0275921 A1 | 11/2011 | Revishvili | |
| 2012/0184863 A1 | 7/2012 | Harlev et al. | |
| 2012/0184865 A1 | 7/2012 | Harlev | |
| 2013/0281870 A1 | 10/2013 | El Haddad et al. | |
| 2013/0338519 A1* | 12/2013 | Chen | A61B 5/7221 600/521 |
| 2014/0155723 A1 | 6/2014 | Levin et al. | |
| 2014/0275919 A1* | 9/2014 | Katra | A61B 5/339 600/374 |
| 2016/0192902 A1 | 7/2016 | Werneth | |
| 2016/0338611 A1 | 11/2016 | Kalinin | |
| 2017/0273588 A1 | 9/2017 | He | |
| 2018/0020939 A1 | 1/2018 | Albert | |

FOREIGN PATENT DOCUMENTS

| | | |
|---|---|---|
| JP | 2001502189 | 2/2001 |
| JP | 2002-224069 | 8/2002 |
| JP | 2012500657 | 1/2012 |
| JP | 2012508079 | 4/2012 |
| JP | 2013-103130 | 5/2013 |
| JP | 2013223730 | 10/2013 |
| WO | 96/005768 A1 | 2/1996 |
| WO | 01/82099 A1 | 11/2001 |

OTHER PUBLICATIONS

Japanese Office Action dated Jul. 14, 2020.
European Extended Search Report dated Sep. 30, 2020 in EP20168416.
Houben R P M et al: "Automatic mapping of human atrial fibrillation by template matching", Heart Rhythm Elsevier, US vol. 3, No. 10, Oct. 1, 2006 (Oct. 1, 2006 pp. 1221-1228.
Hnatkova K el al: "A computer package generating non-invasive atrial electrograms: detection and subtraction of QRS and T waves", Computers in Cardiology 1998 Cleveland, OH, USA Sep. 13-16, 1998 (Sep. 13, 1998) pp. 553-536.
JP2002224069A—Description and original document with drawings.
Japanese Office Action dated Sep. 11, 2018.
European Search Report for Application No. EP15152852.
U.S. Appl. No. 61/932,877, filed Jan. 29, 2014.
U.S. Appl. No. 14/166,982, filed Jan. 29, 2014.
Australia Divisional application No. 2020267161, Examination Report dated Mar. 11, 2021.
AU2020267161—Examination Report No. 3 dated Jun. 8, 2021.
Shah et al., QRS Subtraction and the ECG Analysis of Atrial Ectopics' Ann Noninvasive Electrocardiol. Oct. 2004. vol. 9. No. 4. pages 389-398.
Venkatachalam et al., 'Signals and signal processing for the electrophysiologist Part II: signal processing and artifact' Circ ArrhythmElectrophysiol. Dec. 2011. vol. 4. No. 6 pp. 974-981.

* cited by examiner

DOUBLE BIPOLAR CONFIGURATION FOR ATRIAL FIBRILLATION ANNOTATION

CROSS-REFERENCE TO RELATED APPLICATIONS

This Application is a Divisional of U.S. patent application Ser. No. 15/380,340, filed Dec. 15, 2016, now U.S. Pat. No. 10,238,309, issued Mar. 26, 2019, which is a Continuation of U.S. patent application Ser. No. 14/585,828, filed Dec. 30, 2014, now U.S. Pat. No. 9,554,718 patent, issued Jan. 31, 2017, which claims priority to U.S. Provisional Application No. 61/932,877, filed 29 Jan. 2014, which is herein incorporated by reference.

BACKGROUND OF THE INVENTION

1. Field of the Invention

This invention relates to cardiac physiology. More particularly, this invention relates to the evaluation of electrical propagation in the heart.

2. Description of the Related Art

TABLE 1

| Acronyms and Abbreviations | |
|---|---|
| CFAE | Complex Fractionated Atrial Electrogram |
| ECG | Electrocardiogram |
| EGM | Electrogram |
| FIR | Finite Infinite Response |
| IIR | Infinite Impulse Response |
| LAT | Local Activation Time |
| WCT | Wilson Central Terminal |

Cardiac arrhythmias such as atrial fibrillation are an important cause of morbidity and death. Commonly assigned U.S. Pat. Nos. 5,546,951, and 6,690,963, both issued to Ben Haim and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. Nos. 6,226,542 and 6,301,496, both issued to Reisfeld, which are incorporated herein by reference. As indicated in these patents, location and electrical activity is typically initially measured on about 10 to about 20 points on generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a multiple-electrode catheter to measure electrical activity at multiple points in the heart chamber simultaneously. A record derived from time varying electrical potentials as measured by one or more electrodes is known as an electrogram. Electrograms may be measured by unipolar or bipolar leads, and are used, e.g., to determine onset of electrical propagation at a point, known as local activation time.

However, determination of local activation time as an indicator of electrical propagation becomes problematic in the presence of conduction abnormalities. For example, atrial electrograms during sustained atrial fibrillation have three distinct patterns: single potential, double potential and a complex fractionated atrial electrograms (CFAE's). Thus, compared to a normal sinus rhythm signal, an atrial fibrillation signal is extremely complex, as well as being more variable. While there is noise on both types of signal, which makes analysis of them difficult, because of the complexity and variability of the atrial fibrillation signal the analysis is correspondingly more difficult. On the other hand, in order to overcome the atrial fibrillation in a medical procedure, it is useful to establish possible paths of activation waves travelling through the heart representing atrial fibrillation. Once these paths have been identified, they may be blocked, for example, by appropriate ablation of a region of the heart. The paths may be determined by analysis of intra-cardiac atrial fibrillation signals, and embodiments of the present invention facilitate the analysis.

SUMMARY OF THE INVENTION

While the description herein is, for simplicity, directed to situations where atrial fibrillation is occurring, those having ordinary skill in the art will be able to adapt the description, mutatis mutandis, for other types of fibrillation.

Embodiments of the present invention simultaneously acquire electropotential signals in the heart using a catheter having a multiplicity of electrodes at its distal end, each electrode generating a respective unipolar signal. The signals may be considered as unipolar signals, or in combination with another electrode, as bipolar signals. Unipolar signals may be calculated with respect to the Wilson central terminal (WCT), or with respect to another intracardiac electrode.

In a first part of the analysis of the signals, significant features, typically sections of the signals having a large numerical slope, are identified. The analysis is performed for the unipolar signals (using the bipolar signals to improve the analysis). The analysis identifies the electrical activations, herein termed annotations, and assigns respective quality factors to each of the annotations.

In a second part of the analysis, the atrial fibrillation signals are further investigated to identify blocked regions of the heart, i.e., regions of the heart where cells have been temporarily saturated (refractory), so that they are unable to sustain, or are only partly able to sustain, passage of an activation wave and subsequent detection of annotations. The analysis can identify cells that are permanently non-conducting, such as cells of scar tissue.

The results of the two parts of the analysis may be incorporated into a dynamic 3D map of the heart, showing progress of the activation wave through the heart, as well as blocked regions of the heart, i.e., regions through which an activation wave does not pass.

There is provided according to embodiments of the invention a method, which is carried out by inserting a probe having electrodes into a heart of a living subject, recording a bipolar electrogram and a unipolar electrogram from one of the electrodes at a location in the heart, and defining a time interval including a window of interest wherein a rate of change in a potential of the bipolar electrogram exceeds a predetermined value. The method is further carried out by establishing an annotation in the unipolar electrogram, wherein the annotation denotes a maximum rate of change in a potential of the unipolar electrogram within the window of interest, assigning a quality value to the annotation, and generating a 3-dimensional map of a portion of the heart that includes the annotation and the quality value thereof.

According to another aspect of the method, recording a bipolar electrogram includes establishing a double bipolar electrode configuration of electrodes. The double bipolar electrode configuration includes a first differential signal from a first pair of unipolar electrodes and a second differential signal from a second pair of unipolar electrodes, wherein the bipolar electrogram is measured as a time-varying difference between the first differential signal and the second differential signal.

According to still another aspect of the method, establishing an annotation includes computing a wavelet transform of the unipolar electrogram.

An additional aspect of the method includes producing a scalogram of the wavelet transform and determining the maximum rate of change in the scalogram.

Yet another aspect of the method includes determining from the quality value that the annotation is a qualified annotation that meets predetermined blocking criteria, and indicating on the map that the qualified annotation is at or near a blocked region of the heart.

According to still another aspect of the method, establishing an annotation includes removing ventricular far field components from the unipolar electrogram.

According to one aspect of the method, establishing an annotation includes determining if a temporal cycle length of the unipolar electrogram at the annotation lies within predefined statistical bounds for temporal cycle lengths of other annotations.

An additional aspect of the method includes adjusting the quality value of the annotation according to at least one of a quality value, inter-annotation distance and timing of another annotation.

According to another aspect of the method, the other annotation was generated from another unipolar electrogram that was read from another of the electrodes.

A further aspect of the method includes filtering the unipolar electrogram by an amount sufficient to reduce noise to a predetermined level, wherein assigning a quality value includes determining the amount.

There is further provided according to embodiments of the invention an apparatus, including an intra-body probe having a plurality of electrodes. The probe is configured to contact tissue in a heart. The apparatus includes a display, and a processor, which is configured to receive an electrical signal from the electrodes and to perform the steps of recording a bipolar electrogram and a unipolar electrogram from one of the electrodes at a location in the heart, defining a time interval including a window of interest wherein a rate of change in a potential of the bipolar electrogram exceeds a predetermined value, establishing an annotation in the unipolar electrogram, wherein the annotation denotes a maximum rate of change in a potential of the unipolar electrogram within the window of interest, assigning a quality value to the annotation, and generating on the display a 3-dimensional map of a portion of the heart wherein the map includes the annotation and the quality value thereof.

According to a further aspect of the apparatus, the probe has multiple rays, and each of the rays has at least one electrode.

According to one aspect of the apparatus, the probe is a basket catheter having multiple ribs, and each of the ribs has at least one electrode.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.
Definitions.

"Annotations" or "annotation points" refer to points or candidates on an electrogram that are considered to denote events of interest. In this disclosure the events are typically onset (local activation time) of the propagation of an electrical wave as sensed by the electrode.

"Activity" in an electrogram is used herein to denote a distinct region of bursty or undulating changes in an electrogram signal. Such a region may be recognized as being outstanding between regions of baseline signals. In this disclosure "activity" more often refers to a manifestation on an electrogram of one or more electrical propagation waves through the heart.

Figure 1:
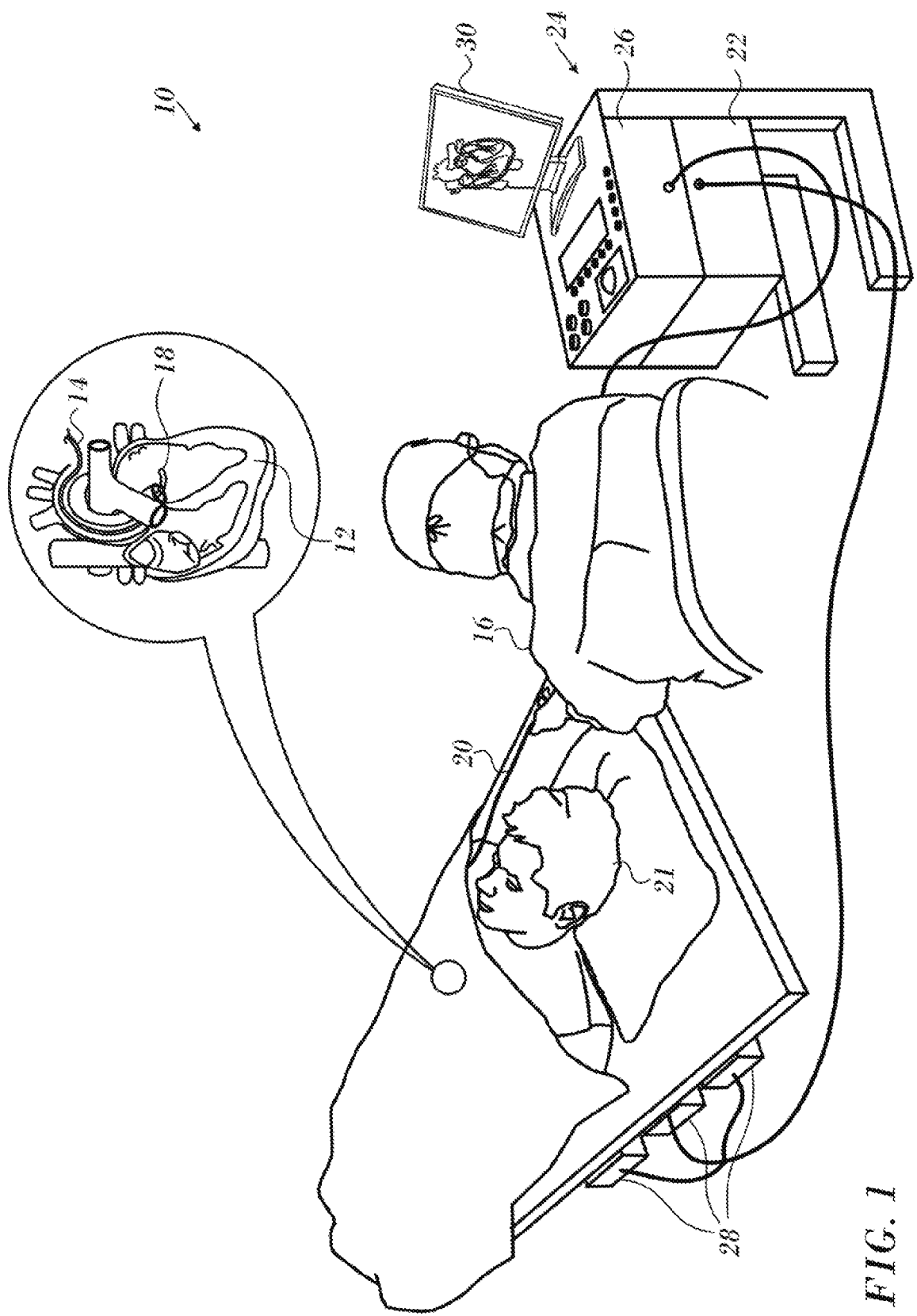
FIG. 1 is a pictorial illustration of a system for detecting areas of abnormal electrical activity in a heart of a living subject in accordance with an embodiment of the invention.

Turning now to the drawings, reference is initially made to FIG. 1, which is a pictorial illustration of a system 10 for detecting areas of electrical activity in a heart 12 of a living subject 21 in accordance with a disclosed embodiment of the invention. The system comprises a probe, typically a catheter 14, which is percutaneously inserted by an operator 16, who is typically a physician, through the patient's vascular system into a chamber or vascular structure of the heart. The operator 16 brings the catheter's distal tip 18 into contact with the heart wall at a target site that is to be evaluated. Unipolar and bipolar electrograms are recorded using mapping electrodes on the distal segment of the catheter. Electrical activation maps based on the electrograms are then prepared, according to the methods disclosed in the above-noted U.S. Pat. Nos. 6,226,542, and 6,301,496, and in commonly assigned U.S. Pat. No. 6,892,091, whose disclosure is herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic.

The catheter 14 typically comprises a handle 20, having suitable controls on the handle to enable the operator 16 to steer, position and orient the distal end of the catheter as desired to the ablation. To aid the operator 16, the distal portion of the catheter 14 contains position sensors (not shown) that provide signals to a positioning processor 22, located in a console 24. The catheter 14 may be adapted, mutatis mutandis, from the ablation catheter described in commonly assigned U.S. Pat. No. 6,669,692, whose disclosure is herein incorporated by reference. The console 24 typically contains an ECG processor 26 and a display 30.

The positioning processor 22 measures location and orientation coordinates of the catheter 14. In one embodiment, the system 10 comprises a magnetic position tracking system that determines the position and orientation of the catheter 14. The system 10 typically comprises a set of external radiators, such as field generating coils 28, which are located in fixed, known positions external to the patient. The coils 28 generate electromagnetic fields in the vicinity of the heart 12. These fields are sensed by magnetic field sensors located in the catheter 14.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. The system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 or cooling an ablation site may be provided.

One system that embodies the above-described features of the system 10 is the CARTO® 3 System, available from Biosense Webster, Inc., 3333 Diamond Canyon Road, Diamond Bar, Calif. 91765. This system may be modified by those skilled in the art to embody the principles of the invention described herein. Multi-electrode basket and spline catheters are known that are suitable for obtaining unipolar and bipolar electrograms. An example of such a spline catheter is the Pentaray® NAV catheter, available from Biosense Webster.

Figure 2:
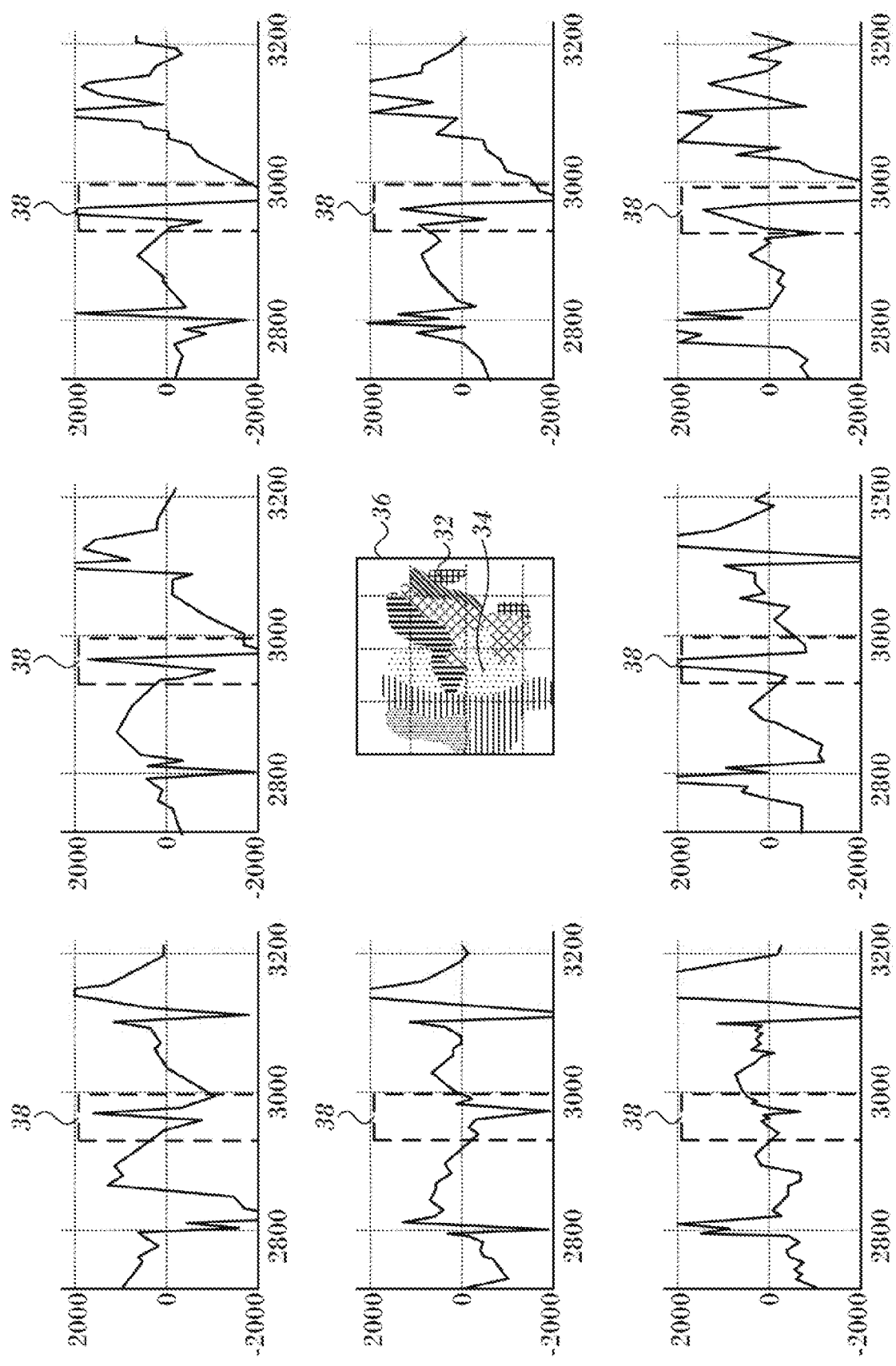
FIG. 2 is a group of bipolar electrograms, in accordance with an embodiment of the invention.

In order to better illustrate the difficulties that can be solved by application of the principles of the invention, reference is now made to FIG. 2, which is a group of bipolar electrograms, in accordance with an embodiment of the invention, in which a simulated bipolar electrode has been positioned in eight directions. The bipolar electrograms have been calculated from the difference of unipolar electrograms e.g., squares 32, 34, shown in distinctive hatching patterns in an electroanatomic map 36, in which one pole is fixedly positioned at the square 32 and the other pole is rotated in 8 steps (4 perpendicular and four oblique positions) around the position of the fixed pole. On the map 36, an activation wave propagates slightly obliquely from right to left. The morphology observed from the eight bipolar complexes differs. This group shows a complex activation, resulting from fusion of two waves, which leads to large differences in morphology and amplitude of the bipolar complexes within windows of interest 38. FIG. 2 illustrates ambiguities in detection of activation. The local activation time at which the activation wave passes a point is calculated by locating an event on an electrogram meeting criteria to be described below and subtracting the time of a fiducial reference from the time of the event. The time of the reference event may be defined using another intracardiac signal or body surface electrocardiogram.

Figure 3:
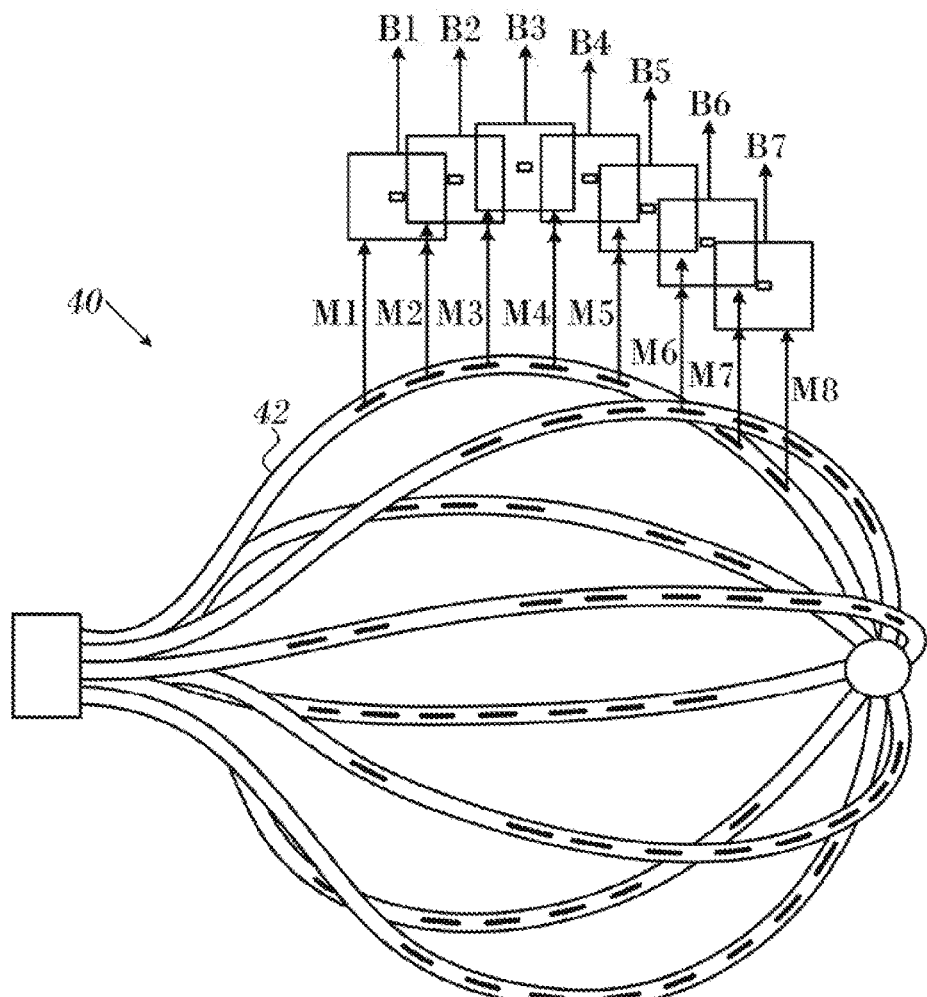
FIG. 3 is a diagram of a basket cardiac chamber mapping catheter for use in accordance with an embodiment of the invention.

The following two figures are schematic illustrations of distal ends of catheters used to acquire electropotentials from the heart, according to an embodiment of the present invention:

Reference is now made to FIG. 3, which is a diagram of a basket cardiac chamber mapping catheter 40 for use in accordance with an embodiment of the invention. The catheter 40 is similar in design to the basket catheter described in U.S. Pat. No. 6,748,255, to Fuimaono, et al., which is assigned to the assignees of the present invention and herein incorporated by reference. The catheter 40 has multiple ribs, each rib having at multiple electrodes. In one embodiment the catheter 40 has 64 unipolar electrodes, and can be configured with up to 7 bipolar pairs per spline. For example rib 42 has unipolar electrodes M1-M8, with bipolar configurations B1-B7. The inter-electrode distance is 4 mm.

Figure 4:
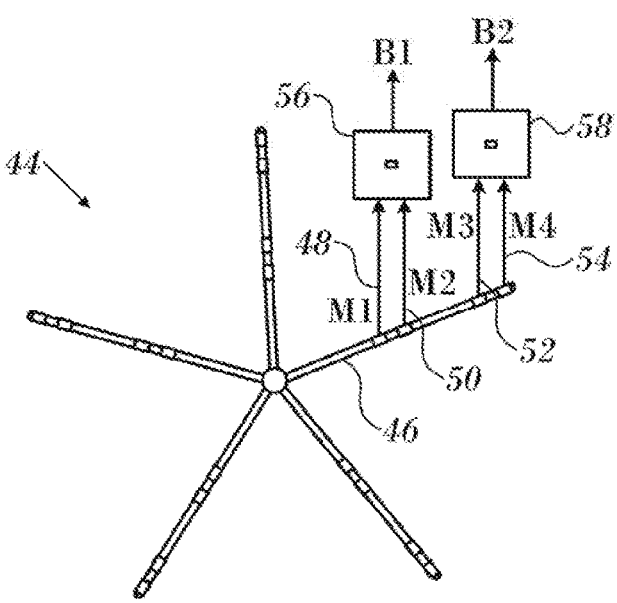
FIG. 4 is a diagram of a spline catheter for use in accordance with an embodiment of the invention.

Reference is now made to FIG. 4, which is a diagram of a spline catheter 44 for use in accordance with an embodiment of the invention. An example of such a spline catheter is the Pentaray® NAV catheter, available from Biosense Webster. The catheter 44 has multiple splines, each spline having several electrodes. In one embodiment the catheter 44 has 20 unipolar electrodes, which can be configured as either two or three bipolar pairs per spline. For example, spline 46 has a first pair of unipolar electrodes 48, 50 and a second pair of unipolar electrodes 52, 54 (M1-M4). Respective differences between the unipolar electrode pairs are calculated in blocks 56, 58. The outputs of blocks 56, 58 (B1, B2) can be associated with one another to constitute a hybrid bipolar electrode configuration, an arrangement referred to herein as a "double bipolar configuration". The double bipolar configuration is used to establish a bipolar window of interest as described below. Possible inter-electrode distances are 4-4-4 or 2-6-6 mm. Similar bipolar configurations can be established in the catheter 40 (FIG. 3).

Both of the catheters 38, 44 have multiple electrodes and are examples of distal ends with multiple electrodes in their individual splines, spokes or branches, and the distal ends may be inserted into the heart of a patient. Embodiments of the present invention use catheters such as the catheters 38, 44 to acquire time-varying electropotentials simultaneously from different regions of the heart. In the case where the heart may be undergoing atrial fibrillation the acquired electropotentials are analyzed in order to characterize their transit within the heart.

Figure 5:
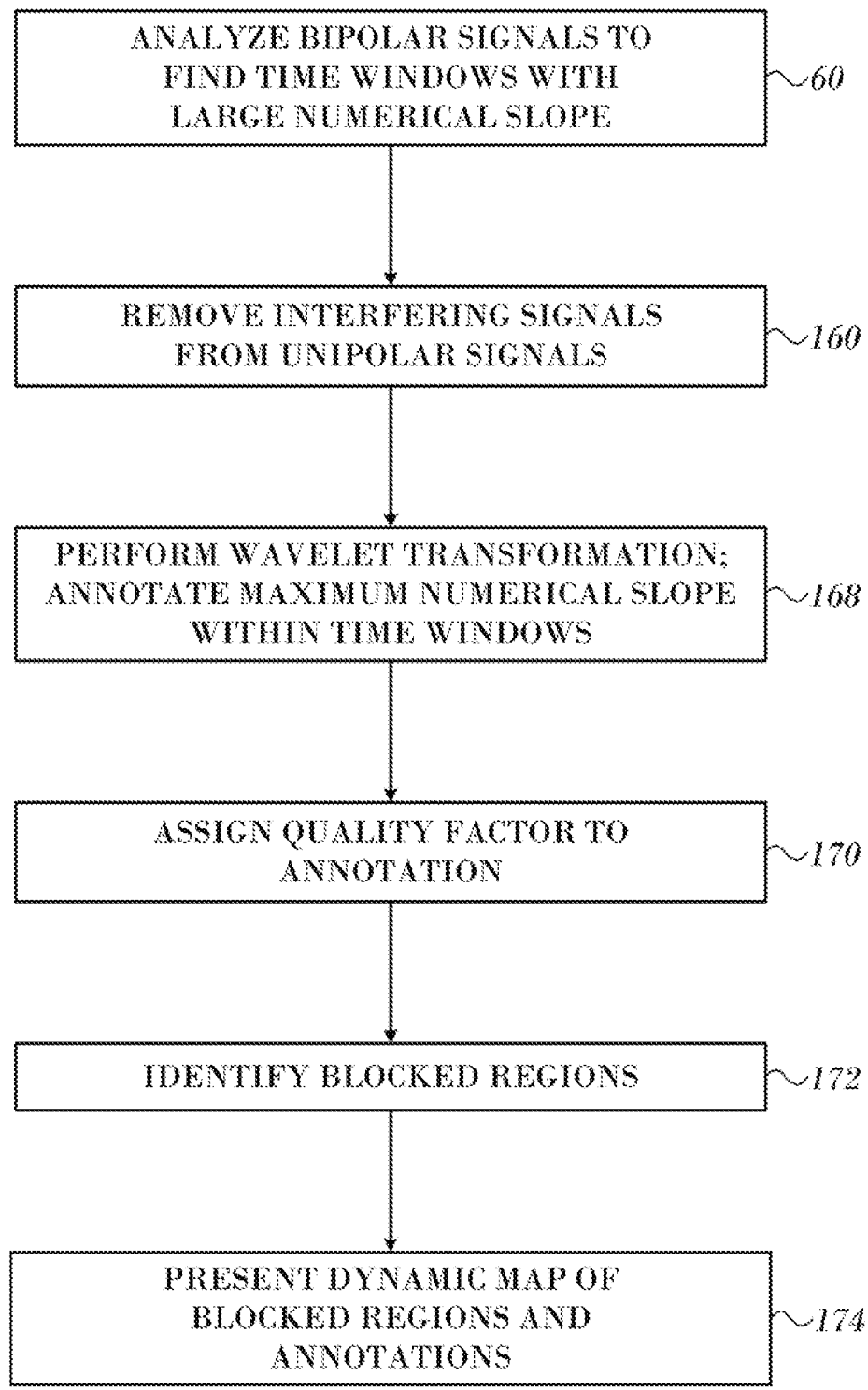
FIG. 5 is a flow chart of a method of annotating an electroanatomic map of the heart in accordance with an embodiment of the invention.

Reference is now made to FIG. 5, which is a flow chart of a method of annotating an electroanatomic map of the heart in accordance with an embodiment of the invention. The process steps are shown in a particular linear sequence for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

The method comprises analyzing the electropotentials acquired by multiple catheter electrodes while the subject is experiencing a conduction disturbance, e.g., atrial fibrillation. Initially electropotential signals are acquired as bipolar potentials plotted over time, typically by finding the differential signal between pairs of adjacent electrodes. However, there is no necessity that the pairs of electrodes be adjacent, and in some embodiments bipolar signals from non-adjacent electrodes are used. For the bipolar signals information on the 3-dimensional position of the electrodes may be used; alternatively or additionally information on the electrode arrangement in the catheter may be used.

In initial step 60 the bipolar signals are analyzed to determine initial time periods, or windows, during which there is a relatively large change in potential, i.e., a maximum value of $$\left| \frac{dv}{dt} \right|.$$

Figure 6:
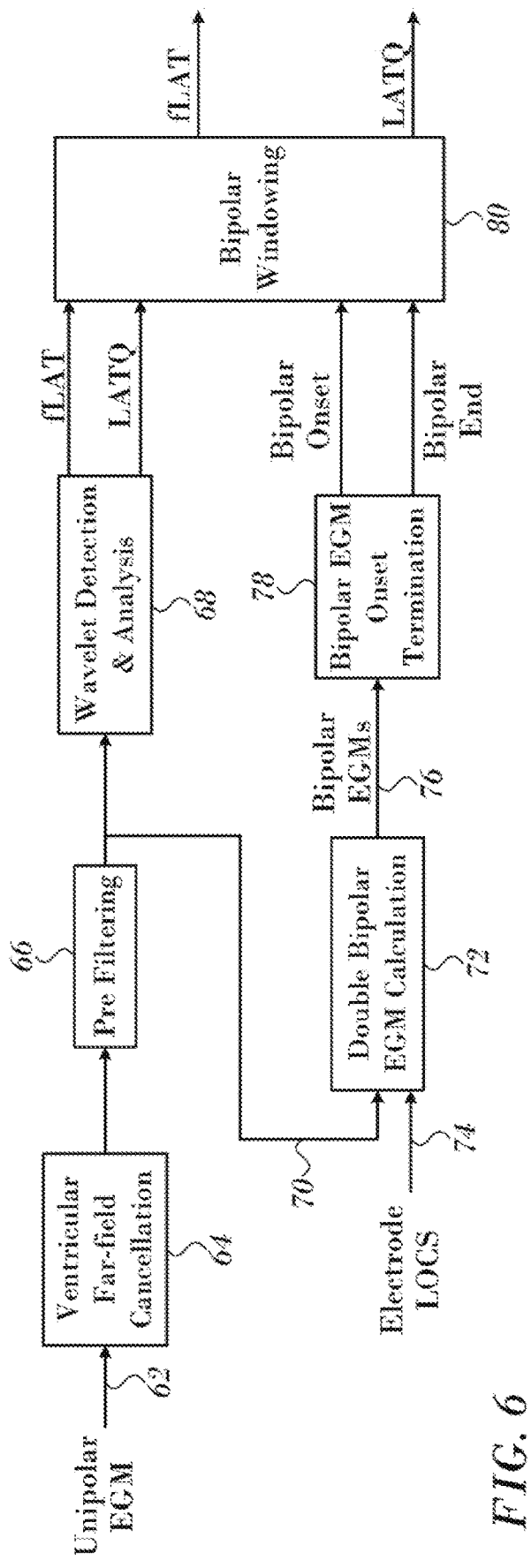
FIG. 6 is a block diagram of unipolar local activation time detection in accordance with an embodiment of the invention.

Reference is now made to FIG. 6, which is a block diagram of a method of unipolar local activation time (LAT) detection in accordance with an embodiment of the invention. A unipolar electrogram (EGM) input 62 is processed for removal of ventricular far field effects in a block 64. Far field reduction can be accomplished using the teachings of commonly assigned application Ser. No. 14/166,982, entitled Hybrid Bipolar/Unipolar Detection of Activation Wavefront, which is herein incorporated by reference. Pre-filtering occurs in block 66, and may be accomplished using high and low pass filters, e.g. FIR and IIR filters. The output of block 66 is then processed in wavelet detection block 68, details of which are described below.

The output of block 66 forms an input 70 of double bipolar electrogram calculation block 72. Another input 74 of block 72 carries the identification of the electrodes being used for calculation of a bipolar electrogram, as an output signal 76. Each member of a bipolar pair is constructed as described with reference to the catheter 44 (FIG. 4). For example the inputs 70, 74 of block 72 could be unipolar electrodes 48, 50 (FIG. 4) of the catheter 44. Block 56 of FIG. 4 corresponds to block 72 of FIG. 6. Bipolar EGM onset and termination are established in block 78. This may be accomplished using the teachings of commonly assigned U.S. Patent Application Publication No. 2013/0281870, which is herein incorporated by reference. Windows of interest for the bipolar electrogram are established using the outputs of block 68 and block 78 in block 80.

Figure 7:
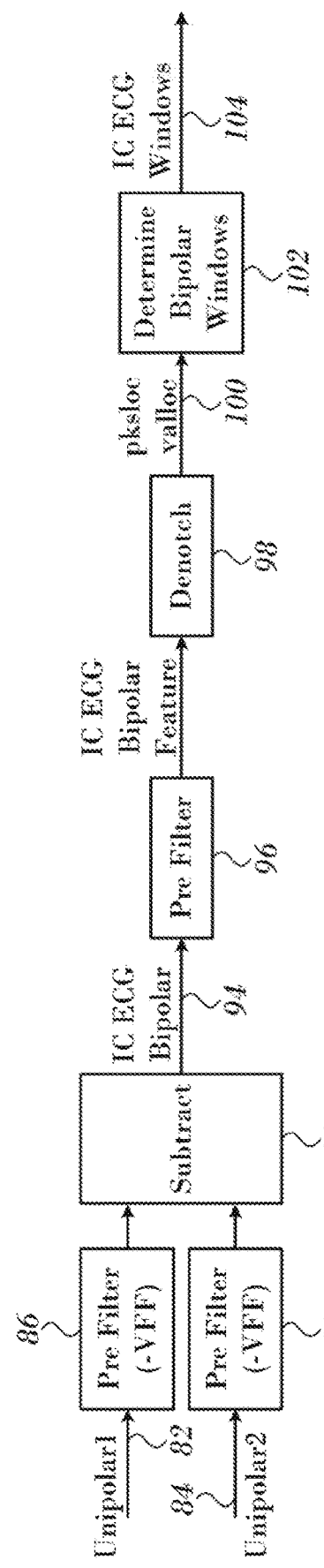
FIG. 7 is a detailed block diagram of an aspect of unipolar local activation time detection shown in FIG. 6.

Reference is now made to FIG. 7, which is a detailed block diagram illustrating the operation of block 72 (FIG. 6) in accordance with an embodiment of the invention. Two EGM inputs 82, 84 are pre-filtered and far-field components removed in blocks 86, 88. The inputs 82, 84 are typically generated from pairs of neighboring electrodes, each member of a pair itself constituting a bipolar source, as shown in FIG. 3 and FIG. 4. For example, the input 82 could be from unipolar electrode 50 (FIG. 4). The outputs of blocks 86, 88 are subtracted in block 92, generating a double bipolar output signal 94. The signal 94 is subjected to another pre-filtering step in block 96, denotched in block 98, and an output signal 100 submitted to block 102 wherein a bipolar window of interest is determined. An output signal 104 is produced by block 102.

Figure 8:
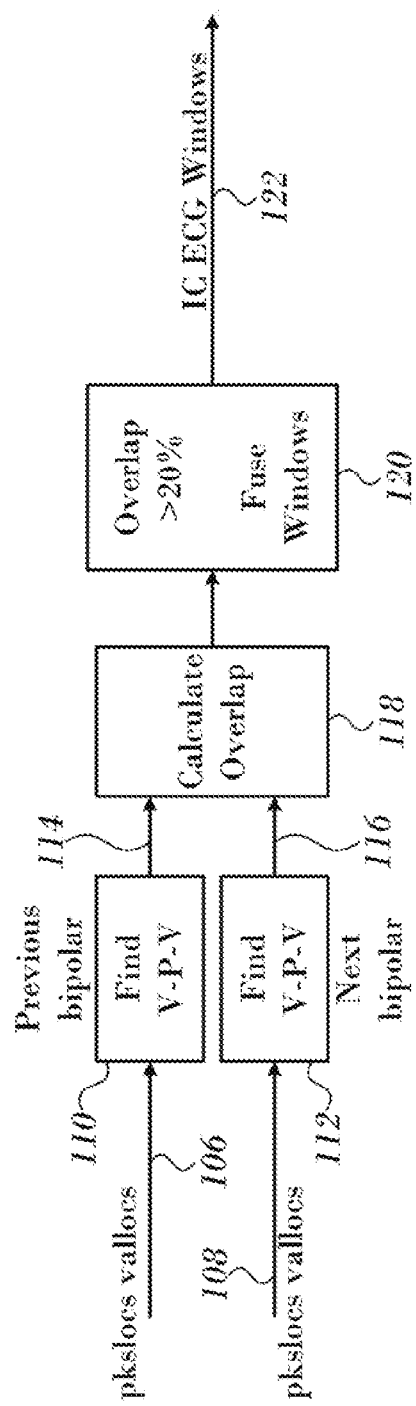
FIG. 8 is a detailed block diagram of the aspect of unipolar local activation time detection shown in FIG. 7.

Reference is now made to FIG. 8, which is a detailed block diagram illustrating a portion of the operation of block 102 (FIG. 7) in accordance with an embodiment of the invention. Signals 106, 108, which represent successive tentative window determinations (signal 104 (FIG. 7)) are evaluated in window detection blocks 110, 112, which generate output signals 114, 116, respectively. A maximum between two minima is detected. The signals 114, 116 are processed in block 118, where overlap of the detected windows is determined. In block 120 the windows found in blocks 110, 112 are fused, provided that there is an overlap that exceeds 20%. A signal 122 indicative of a window of interest is output by block 120.

Figure 9:
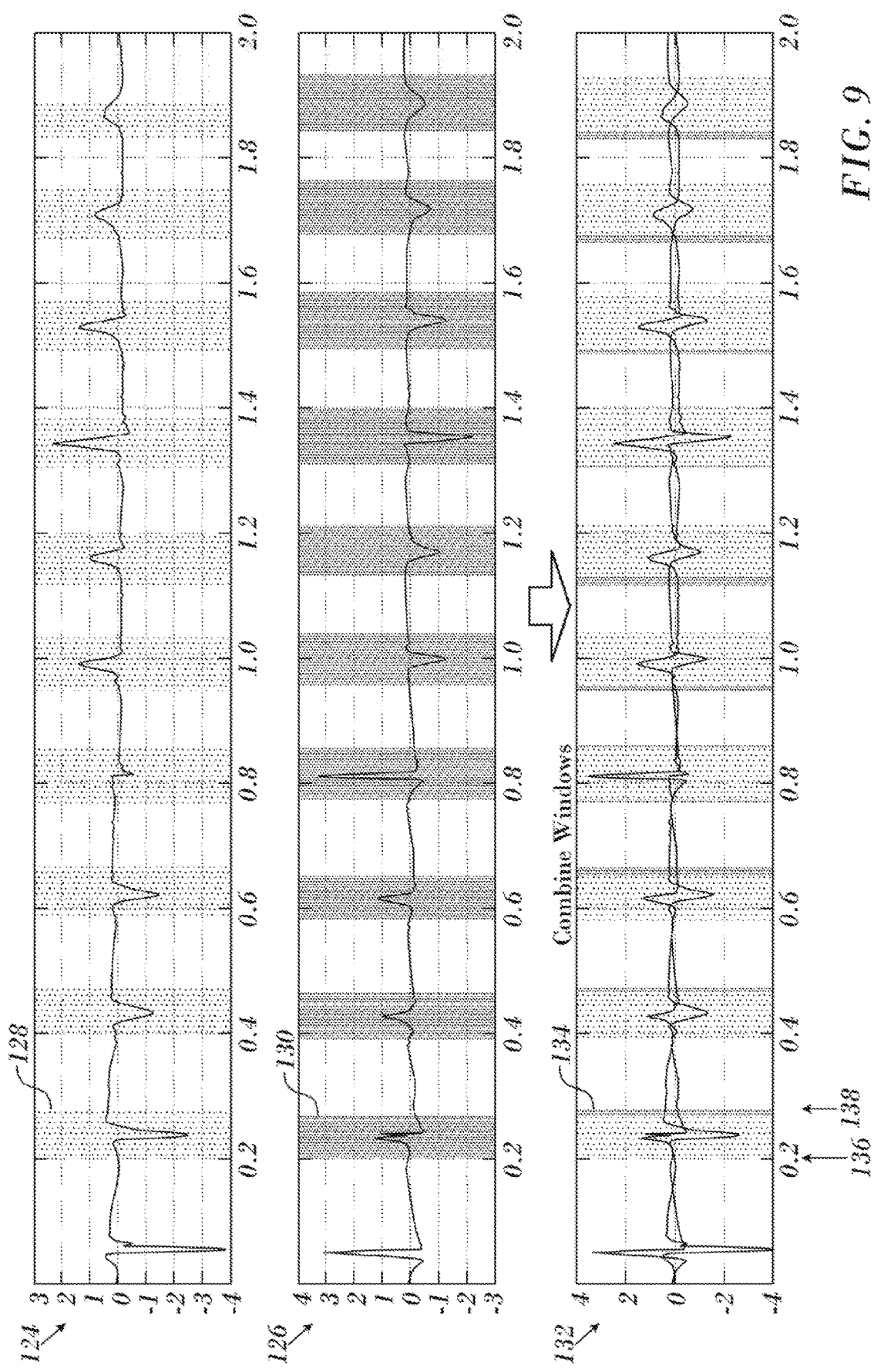
FIG. 9 is a chart illustrating signals that are processed according to the diagram shown in FIG. 8.

Reference is now made to FIG. 9, which is a chart illustrating signals that are processed according to the arrangement of FIG. 8 in accordance with an embodiment of the invention. Graphs 124, 126 represent outputs of blocks 110, 112 and show the morphology of the electrograms and respective detected windows. For example, windows 128, 130 extensively overlap and are therefore fused, as shown in graph 132. Graph 132 indicates a superimposition of the electrograms of the graphs 124, 126 and a fusion of the windows 128, 130 to form a larger window 134. Window 134 begins at point 136, which is the minimum of the onset times of the windows 128, 130 and ends at point 138, which is the maximum of the termination times of the windows 128, 130.

Figure 10:
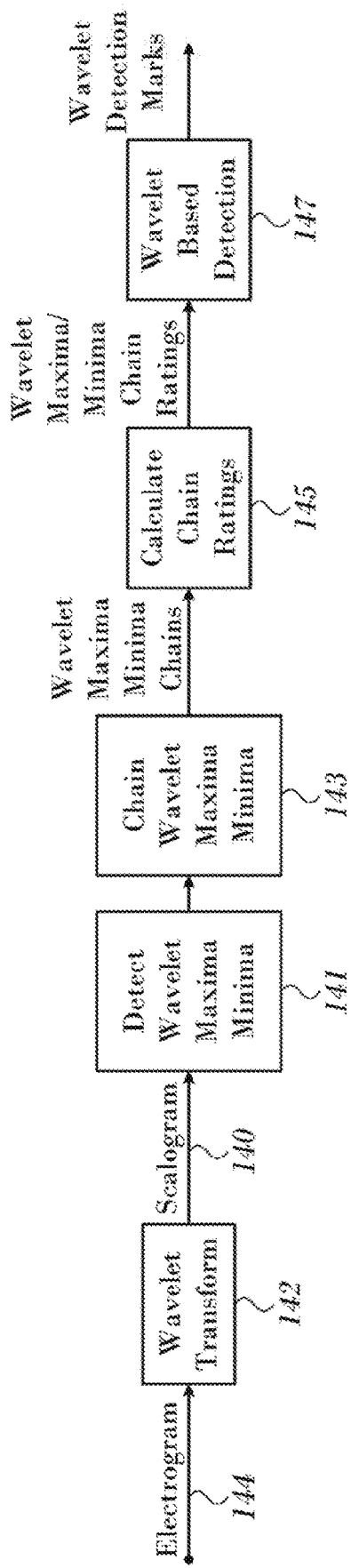
FIG. 10 is a block diagram illustrating wavelet detection in accordance with an embodiment of the invention.

Reference is now made to FIG. 10, which is a detailed block diagram illustrating the operation of wavelet detection block 68 (FIG. 6) in accordance with an embodiment of the invention. Wavelet transformation provides decomposition of a signal as a combination of a set of (orthonormal) basis functions derived from a mother wavelet by dilation and translation. If the wavelet is the derivative of a smoothing function, the wavelet coefficients represent the slope of the input signal. The wavelet parameters used in the arrangement of FIG. 10 comprise: (1) a continuous wavelet transform (CWT); (2) the first derivative of a Gaussian wavelet; and (3) decomposition over 15 linear scales in blocks 141, 143, followed by ratings and peak detection in blocks 145, 147.

Figure 11:
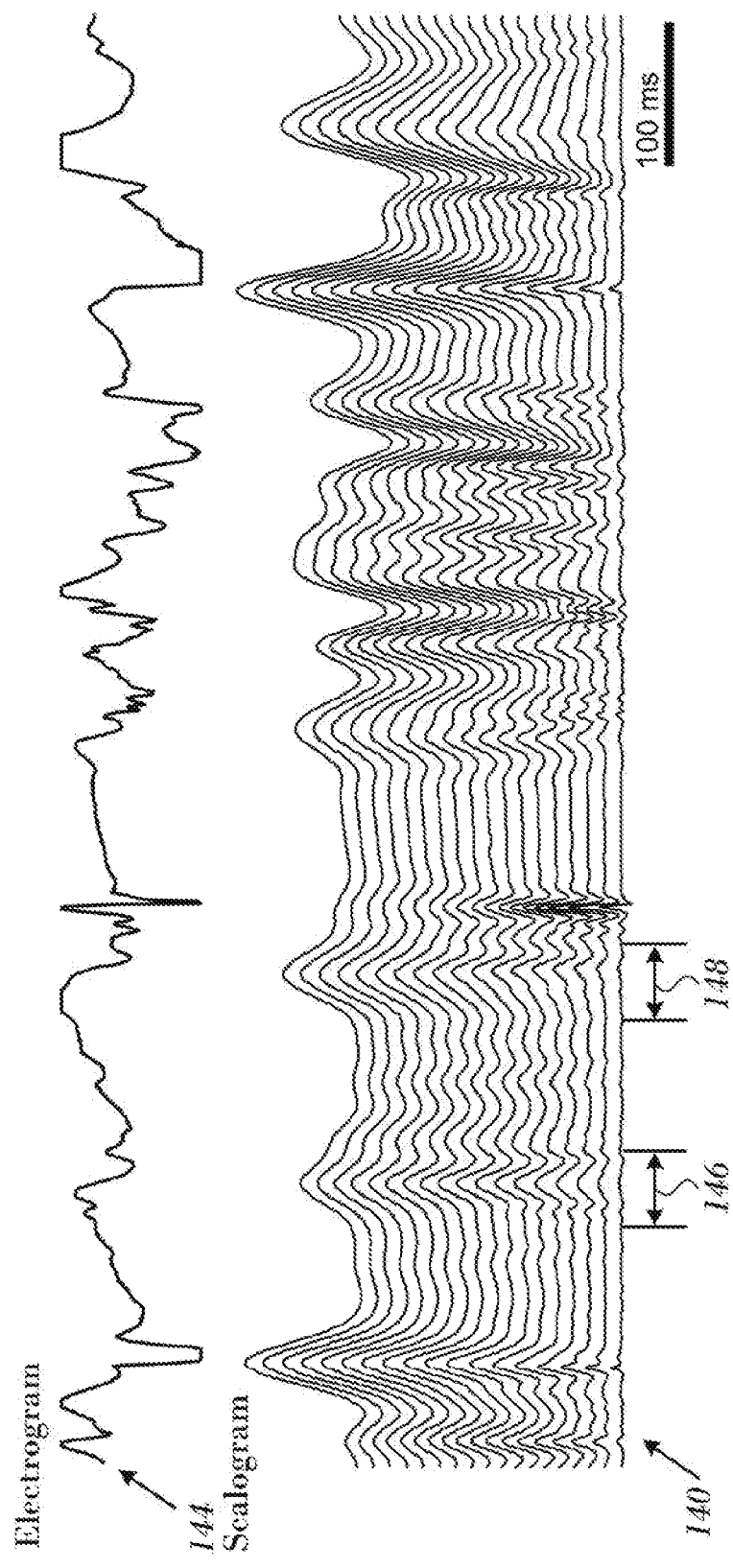
FIG. 11 is a diagram illustrating signals produced by the arrangement shown in FIG. 10 in accordance with an embodiment of the invention.

Reference is now made to FIG. 11, which is a diagram illustrating signals produced by the arrangement shown in FIG. 10 in accordance with an embodiment of the invention. Scalogram 140 is produced in wavelet transform block 142 from electrogram 144 by chaining maxima and minima; i.e., forming an ordered set of curves by an iterative filtering process. Intervals. For example intervals 146, 148 show readily identifiable maxima and minima in the scalogram 140, whereas these are much less distinct in the electrogram 144.

Figure 12:
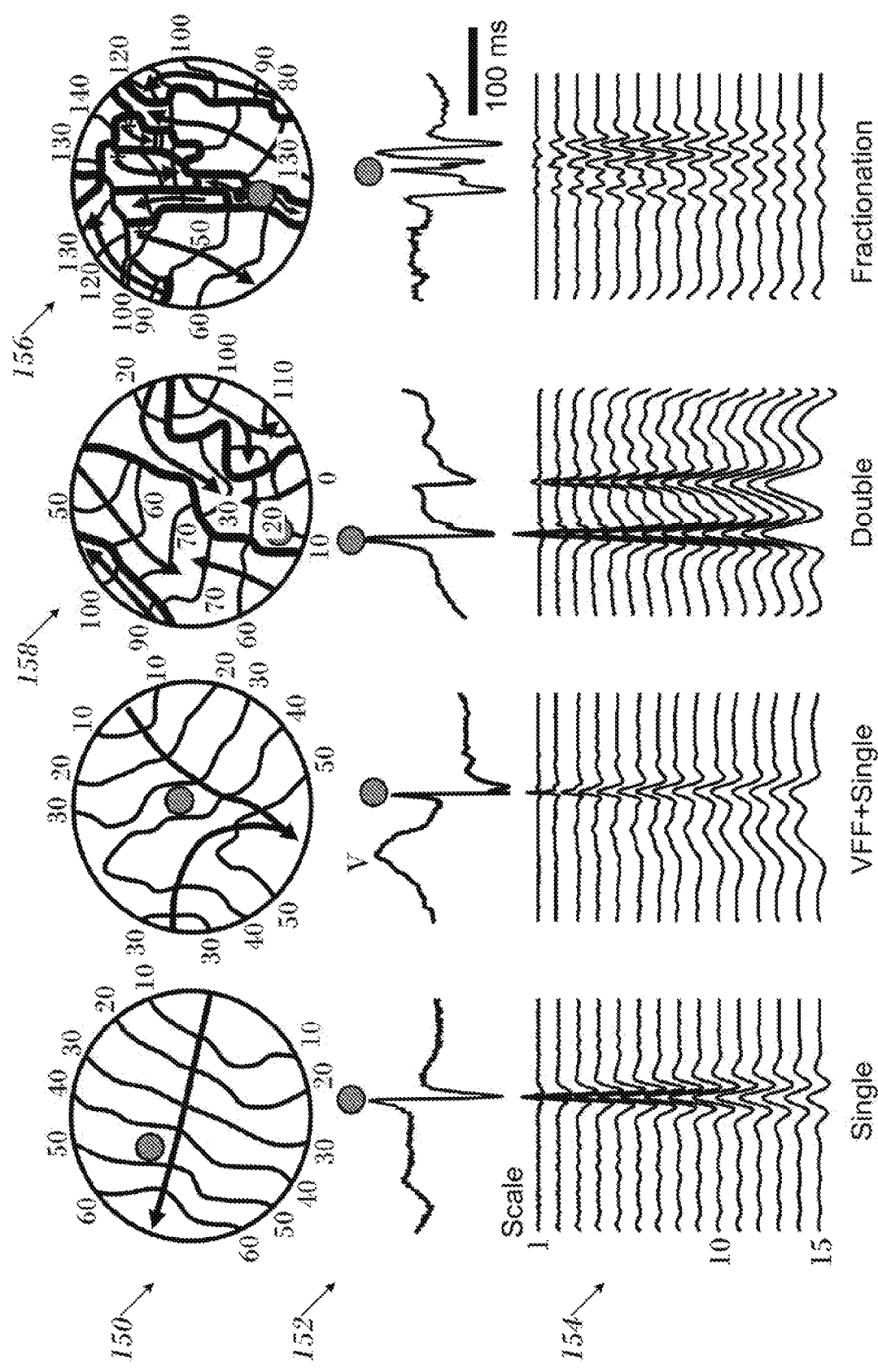
FIG. 12 is a diagram illustrating wavelet transformation in different arrhythmias in accordance with an embodiment of the invention.

Reference is now made to FIG. 12, which is a diagram illustrating the operation of wavelet transform block 68 (FIG. 6) in different arrhythmias in accordance with an embodiment of the invention. Regional electroanatomic maps 150 indicate various types of atrial arrhythmic abnormalities that can be associated with atrial fibrillation. The maps 150 are shown with corresponding electrograms 152 and scalograms 154. The scalograms 154 have distinct morphologies that relate to respective electrograms 152. Generally the peaks in the electrograms 152 are more clearly isolated in the scalograms 154, particularly when the activations become less distinct, for example in the cases 156, 158 at the right of the figure.

Reverting to FIG. 5, in a signal adjustment step 160 interfering signals are removed from the unipolar fibrillation signals, in order to expose the fibrillation signals. The interfering signals include ventricular far field signals or components that are projected from the ventricle. In one way of removing these components, the signal emanating from the ventricle is detected, and a mean QRS signal is subtracted, at the time of generation of the ventricle signal, from the fibrillation signal.

Figure 13:
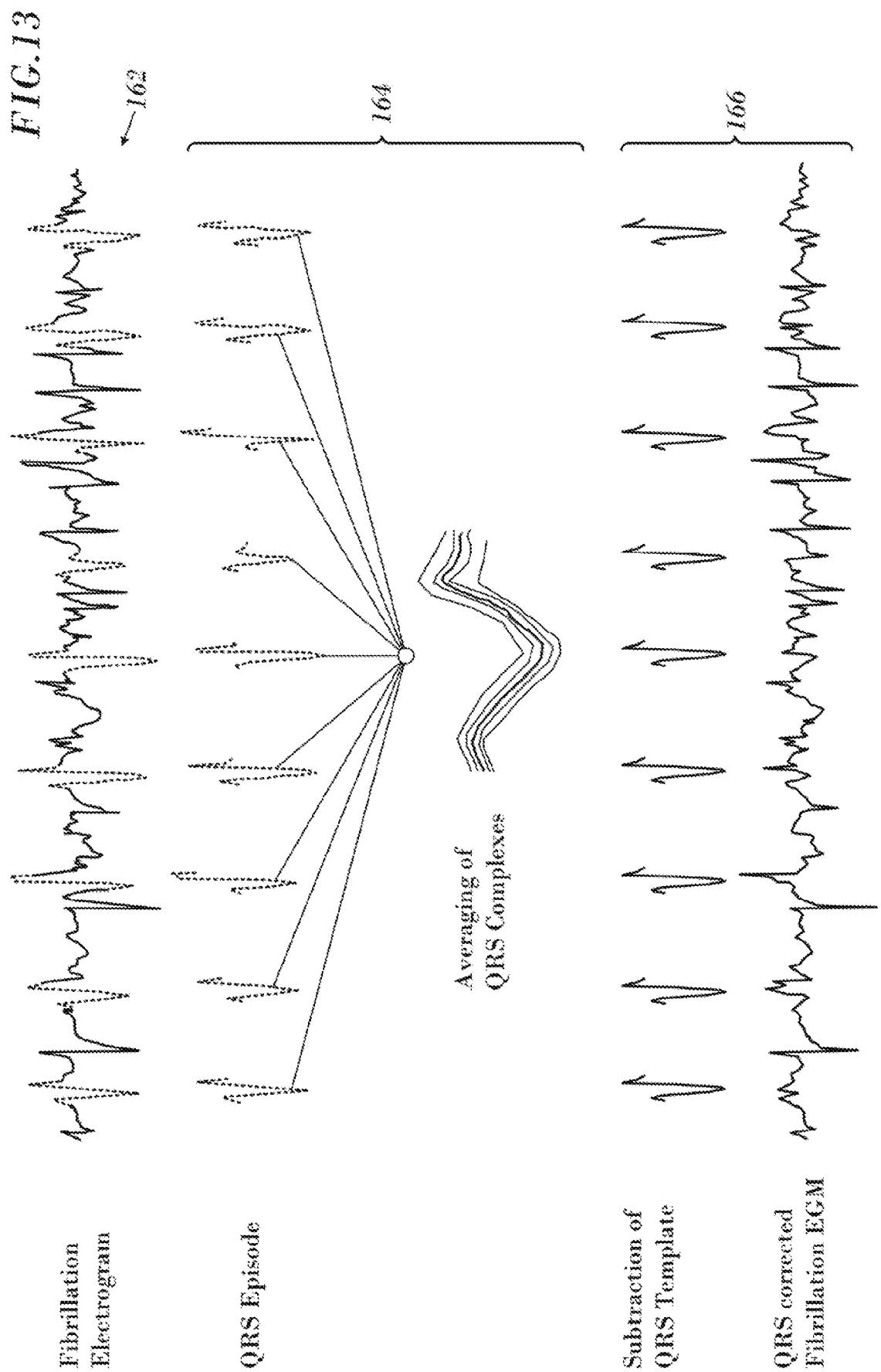
FIG. 13 is a set of diagrams illustrating removal of an interfering signal from a unipolar fibrillation signal in accordance with an embodiment of the invention.

Reference is now made to FIG. 13, which is a set of diagrams illustrating a process for removing an interfering signal from a unipolar fibrillation signal, in accordance with an embodiment of the invention. As shown in a first part 162, a fibrillation signal initially includes a ventricular far-field portion. A mean QRS signal is generated, typically from a set of QRS signals, as is shown in a second part 164, and, as shown in third and fourth parts 166, the fibrillation signal is corrected by subtraction of the mean QRS signal.

Alternatively or additionally, template matching to a predefined ventricle signal, and/or a template based on an estimation from the fibrillation signal, at times where the signal is only ventricular, may be used for prediction of the ventricular far field signal for the unipolar fibrillation signals. Typically, times for expected occurrence of the ventricular signals may be determined from body ECG signals, ventricular intra-cardiac signals, or coronary sinus signals. Using the template, the ventricular far field signals or components may be estimated and subtracted from the fibrillation signal.

Those having ordinary skill in the art will be able to adapt the description above, mutatis mutandis, for other methods of removal of the ventricular far field signal. In addition, interfering signals other than the ventricular far field signals may be removed by similar methods to those described above for the ventricular signals.

Other adjustments that may be performed in the signal adjustments step include noise reduction (including 50/60 Hz signal induced noise), reduction of electro-magnetic interference (EMI), and correcting for baseline drift, by any methods known in the art.

Returning to the flowchart of FIG. 5, in a further analysis step 168 performed on the adjusted unipolar fibrillation signal, times, herein termed annotations, a maximum $$\left|\frac{dv}{dt}\right|$$

value is detected are determined. The process of determining the maximum $$\left|\frac{dv}{dt}\right|$$

value is applied to the adjusted signal within the windows found in the initial analysis initial step 60, and further includes a process of noise reduction. In one embodiment, the noise reduction applied to the corrected fibrillation signal comprises forming a composition of different wavelet transforms with the corrected fibrillation signal. The different wavelet transforms effectively generate filters of differing bandwidths, and the composition of these filters with the corrected fibrillation signal reduces noise in the signal.

Additionally or alternatively, other methods for noise reduction, such as by applying one or more different bandwidth filters to the signal, within the windows referred to above, may be applied to the corrected fibrillation signal.

In a quality estimation step 170, each maximum $$\left|\frac{dv}{dt}\right|$$

annotation may be assigned a parameter measuring the goodness of the annotation, depending on the amount and type of filtering required to determine the annotation in step 168. For example, an annotation assigned with a high parameter value may be returned for both low and high levels of filtering, whereas an annotation assigned with a low parameter value may be returned only for low or high filter levels, but not for both.

The annotations are further characterized to estimate a final quality of the annotation. The characterization is according to the position of the electrodes generating their signal, the location in the heart from where the signal was acquired, the timing of the annotation, the goodness parameter of the annotation (determined in the previous step), and/or whether the annotation is at or close to a time where signal adjustments, described above in the signal adjustment step, have been made. Each of these parameters may be assigned a numerical value. For example, from the position of a first electrode it may be considered that it is physiologically unlikely that the signal acquired by the electrode will comprise an annotation, in which case the annotation final quality may be downgraded. For a second electrode it may be considered likely that the signal comprises an annotation, in which case the annotation final quality may be upgraded.

In addition to the variables described above for estimating the quality of a given annotation, the quality, inter-annotation distance and timing of neighboring spatial annotations may be checked, and the quality of the given annotation adjusted accordingly. For example, if a given electrode is surrounded by electrodes generating annotations with a high quality, then in some cases the quality of the given electrode annotation may be increased (in other cases, described below with reference to step 28, there may be a blocking effect). Alternatively, if a given electrode is surrounded by electrodes generating annotations with a low quality, then the quality of the given electrode annotation may be decreased. In addition, if a given electrode is surrounded by electrodes generating quality annotations significantly outside a physiological range, then the quality of the given electrode may be further decreased.

As a further check to determine the quality of an annotation, the annotation is evaluated with respect to a statistic describing other annotations. For example, a histogram of temporal cycle lengths of each annotation may be generated. Only those annotations lying within predefined bounds of the histogram may be considered to be valid, and those outside the bounds are assumed to be erroneous.

In a blocking identification step 172, the annotations meeting the criteria assigned in step 170 are considered to identify regions of the heart where the activation of the heart muscle appears to have been "blocked." Such a blockage occurs when activation waves collide or are dissociated, causing heart muscle cells at the position of collision to saturate temporarily, so that they are unable to reactivate. These are known as "refractory cells". Blocked regions may be identified by considering the signal on a given electrode, as well as on the surrounding electrodes. Typically, if the annotation signal on the given electrode is significantly smaller, has a different morphology, and/or has a lower quality, than the annotation signals on surrounding electrodes, then the given electrode may be considered to be located at or near a blocked region of the heart. A block may be temporary (functional block) or permanent (e.g., a scar).

In a presentation step 174, the results from the two previous steps, i.e., good quality annotations and regions identified as being blocked, are presented on a dynamic 3-dimensional map of the heart, or a chamber of the heart. Typically, the dynamic map illustrates the relative timing and the quality of the annotations in the heart, as well as an estimated "flow" of the annotations, i.e., time intervals between successive annotations. The dynamic map also illustrates regions of the heart that are assumed to be blocked. The dynamic map may also indicate regions of the heart, or of a chamber of the heart, from which no information was obtained.

Figure 14:
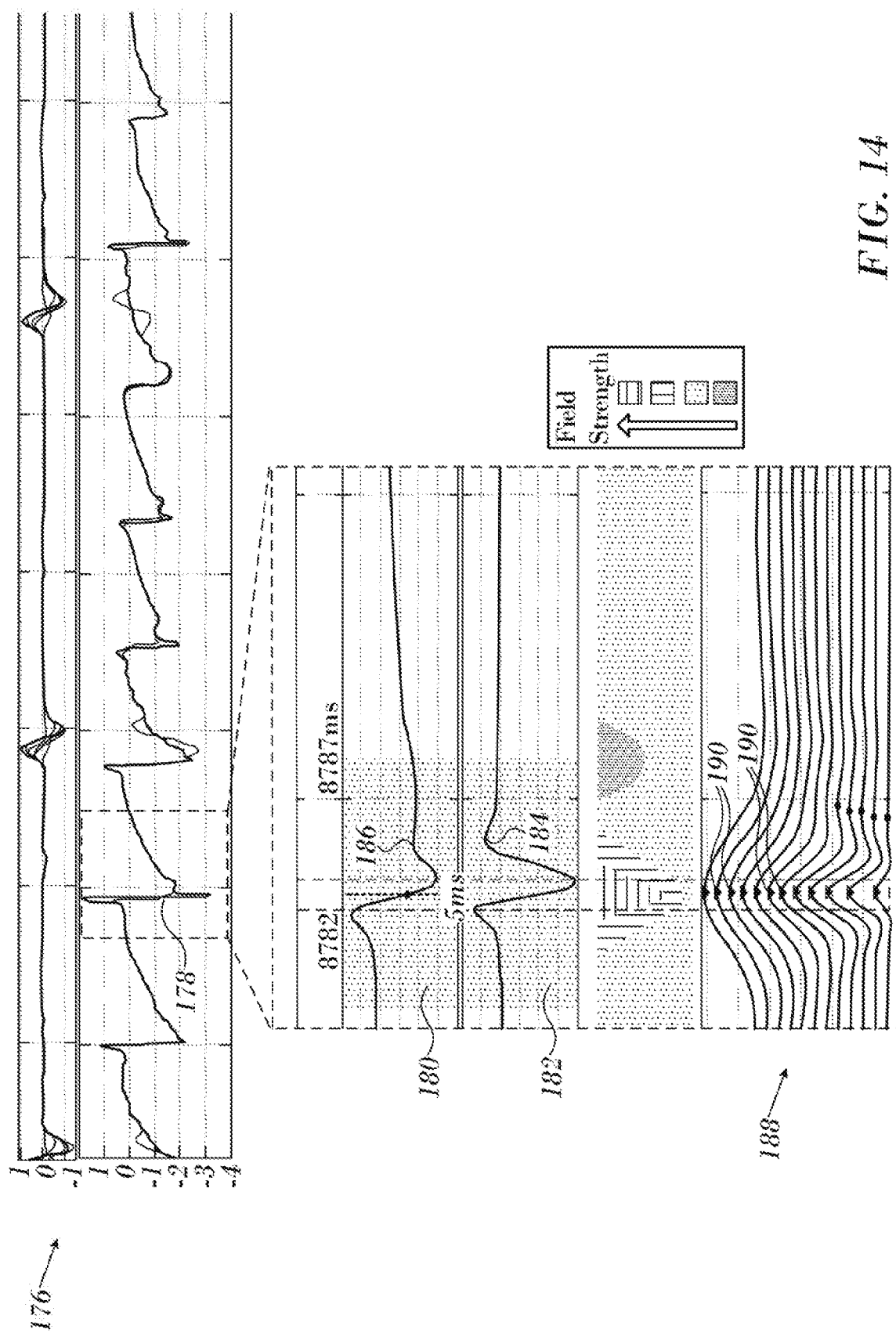
FIG. 14 is a graphic diagram presenting an annotation of an electrogram in accordance with an embodiment of the invention.

Reference is now made to FIG. 14, which is a graphic diagram presenting an annotation of an electrogram 176 in accordance with an embodiment of the invention. The lower portion of the figure details the process applied to a representative complex 178. Hybrid bipolar windows 180, 182 are obtained from two unipolar electrodes as described above. Tracings 184, 186 represent the first derivatives of the signals from the two unipolar electrodes. A scalogram 188 was developed from wavelet transformations computed based on the electrogram 176. A series of annotations 190 is shown on the scalogram 188.

Figure 15:
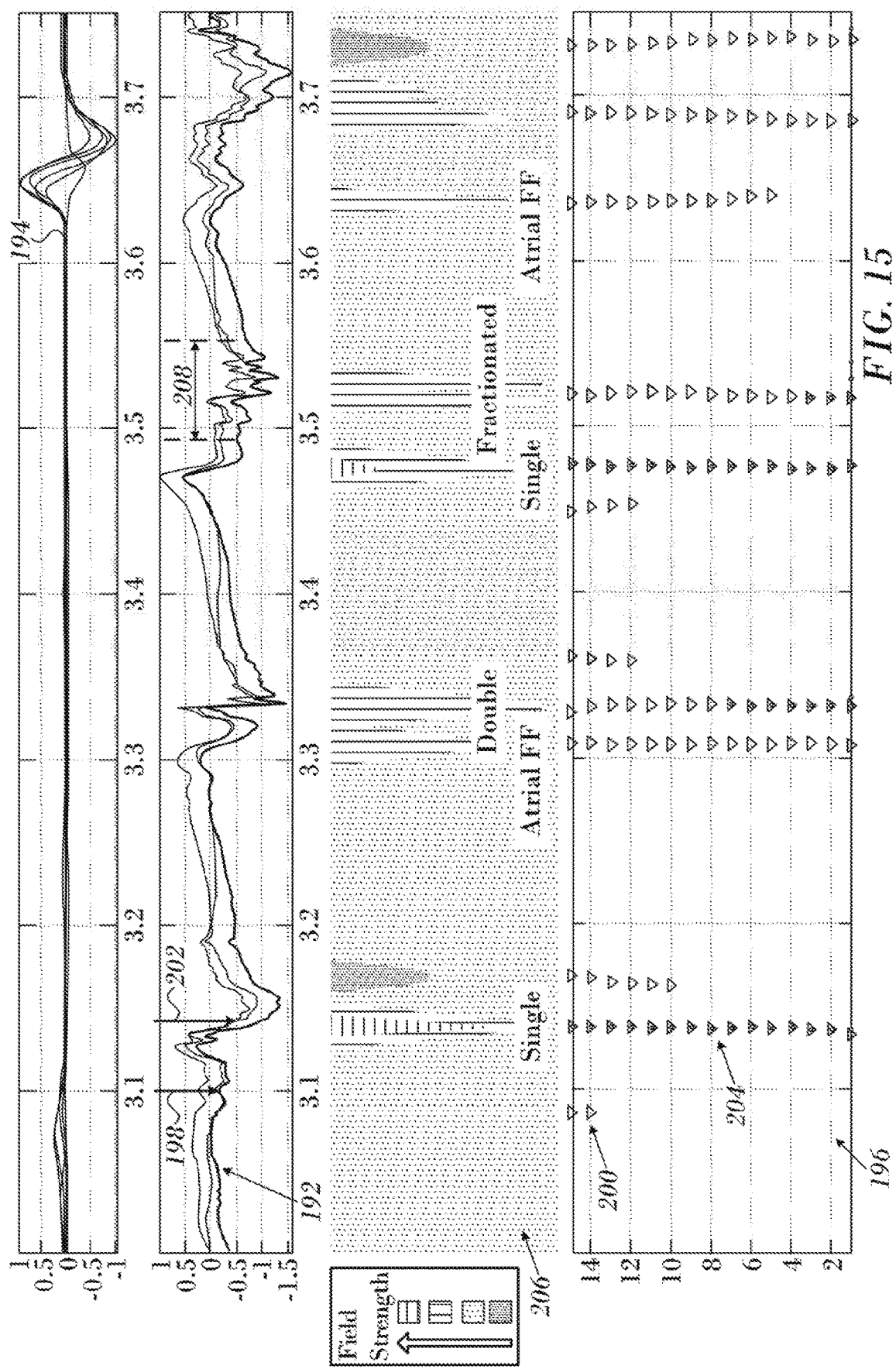
FIG. 15 is a graphic diagram presenting annotations of electrical activity in a case of atrial fibrillation in accordance with an embodiment of the invention.

Reference is now made to FIG. 15, which is a graphic diagram presenting annotations of electrical activity 192 in a case of atrial fibrillation in accordance with an embodiment of the invention. Tracings 194 are superimposed body surface electrode signals. Annotations are shown for several complexes in a scalogram 196 in the lower portion of the figure, and further indicated by the number of triangles in the lower portion of the figure. For example an annotation indicated by arrow 198 is associated with only two triangles 200 and is of relatively low quality compared to an annotation indicated by arrow 202, which is associated with a larger number of triangles 204. The quality of the annotations is further graphically shown in middle portion 206. The technique has successfully annotated a complex fractionated portion 208 of the activity 192.

Figure 16:
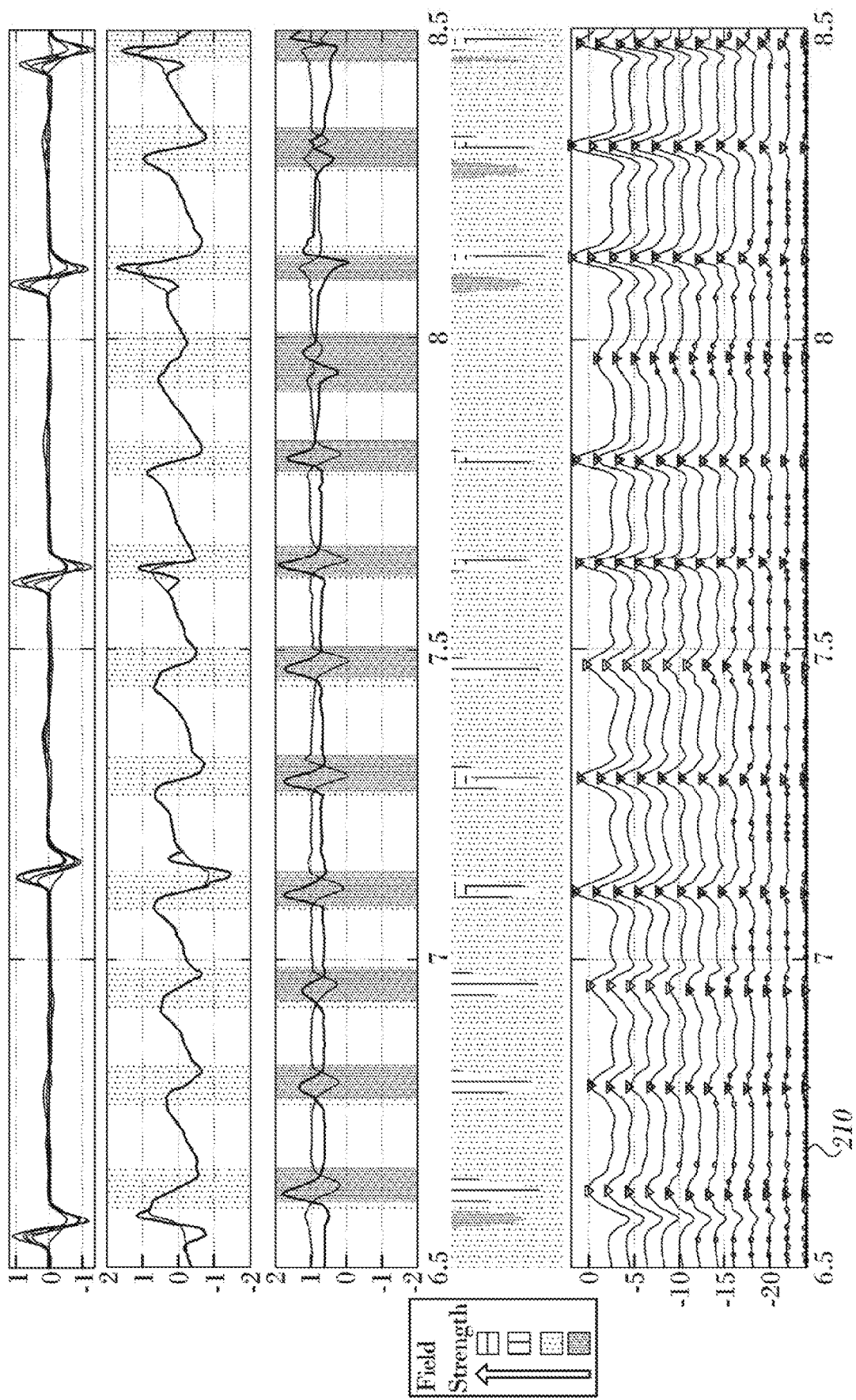
FIG. 16 is a graphic diagram presenting annotations of electrical activity in accordance with an embodiment of the invention.

Reference is now made to FIG. 16, which is a graphic diagram presenting annotations of electrical activity in accordance with an embodiment of the invention. The presentation is similar to FIG. 15. The quality of the annotations is further indicated by dots 210. Dots 210 represent chains starting from the finest scale and progressing to coarser scales. Inspection of the chains indicated by the dots 210 together with the chains indicated by the triangles that progress in the opposite direction permits the operator to distinguish the various activation patterns shown by scalograms 154 (FIG. 12).

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A computer implemented method of determining quality of an annotation comprising:
 receiving an electrogram;
 detecting a plurality of QRS episodes in the electrogram and generating a mean QRS signal from the QRS episodes;
 subtracting the mean QRS signal from the plurality of QRS episodes detected in the electrogram to generate an adjusted electrogram in which potential annotations are exposed;
 identifying an annotation from the adjusted electrogram;
 estimating a quality of the annotation based on one or more parameters selected from:
  an amount and type of filtering required to determine the annotation;
  a position of a unipolar electrode generating its signal;
  a location in the heart from where a signal was acquired;
  a timing of the annotation; or
  whether the annotation is at or close to a time where a signal adjustment has been made; and
 assigning a value to the quality based on the one or more parameters;
 wherein the numerical value of the quality may be upgraded or downgraded based on the likelihood that the one or more parameters indicates an annotation.

2. The computer implemented method of claim 1, wherein for the parameter a position of a unipolar electrode generating its signal, the value is downgraded when, from a position of a first electrode, it is considered physiologically unlikely that a signal from the first electrode will comprise an annotation.

3. The computer implemented method of claim 1, further comprising:
   checking an inter-annotation distance, quality of a neighboring annotation and a timing of neighboring spatial annotations;
   adjusting the value of the quality based on the check.

4. The computer implemented method of claim 3, wherein if a first electrode is surrounded by a plurality of second electrodes that are generating annotations with a high quality value, then the quality value of an annotation from the first electrode is increased.

5. The computer implemented method of claim 3, wherein if a first electrode is surrounded by a plurality of second electrodes generating annotations with a low quality, then the quality of the given electrode annotation may be decreased.

6. The computer implemented method of claim 3, wherein if a first electrode is surrounded by plurality of second electrodes generating annotations significantly outside a predetermined physiological range, then the quality of the given electrode is decreased.

7. The computer implemented method of claim 1, further comprising evaluating the quality of an annotation with respect to a statistic describing other annotations.

8. The computer implemented method of claim 7, wherein the statistic comprises a histogram of temporal cycle lengths of each annotation; and wherein annotations lying within predefined bounds of the histogram are considered to be valid, and those outside the bounds are considered to be erroneous.

* * * * *